(12) United States Patent
Kim et al.

(10) Patent No.: US 12,427,214 B2
(45) Date of Patent: Sep. 30, 2025

(54) WALK-THROUGH QUARANTINE APPARATUS

(71) Applicant: KOREA AIRPORTS CORPORATION, Seoul (KR)

(72) Inventors: Jin Oh Kim, Seoul (KR); Myung Woon Kim, Sejong-si (KR); Jae Ho Jang, Gimpo-si (KR)

(73) Assignee: KOREA AIRPORTS CORPORATION, Seoul (KR)

( * ) Notice: Subject to any disclaimer, the term of this patent is extended or adjusted under 35 U.S.C. 154(b) by 536 days.

(21) Appl. No.: 18/004,259

(22) PCT Filed: Jun. 9, 2021

(86) PCT No.: PCT/KR2021/007211
§ 371 (c)(1),
(2) Date: Jan. 4, 2023

(87) PCT Pub. No.: WO2022/010114
PCT Pub. Date: Jan. 13, 2022

(65) Prior Publication Data
US 2023/0263921 A1      Aug. 24, 2023

(30) Foreign Application Priority Data
Jul. 10, 2020   (KR) .................. 10-2020-0085170

(51) Int. Cl.
*A61L 2/10*     (2006.01)
*A61B 5/01*     (2006.01)
(Continued)

(52) U.S. Cl.
CPC ............... *A61L 2/10* (2013.01); *A61B 5/015* (2013.01); *A61L 2/0047* (2013.01); *A61L 2/14* (2013.01);
(Continued)

(58) Field of Classification Search
CPC ..... A61L 2/10; A61L 2/14; A61L 2/26; A61L 2/0047; A61L 9/20; A61L 9/26;
(Continued)

(56) References Cited

U.S. PATENT DOCUMENTS 7,791,044 B1    9/2010  Taylor et al.
9,198,990 B2 *  12/2015  Fletcher .................... A61L 2/10

FOREIGN PATENT DOCUMENTS

CN      210160081 U    3/2020
CN      111042585 A    4/2020
(Continued)

OTHER PUBLICATIONS

International Search Report issued in PCT/KR2021/007211; mailed Oct. 14, 2021.
(Continued)

*Primary Examiner* — Sean M Luck
(74) *Attorney, Agent, or Firm* — Studebaker Brackett PLLC

(57) ABSTRACT

Disclosed is a walk-through quarantine apparatus which can be installed in passenger gateway facilities, such as airports, ports, and terminals, and multi-use facilities, such as large shopping malls, marts, exhibition halls, and concert halls, so as to sterilize human bodies and belongings. The walk-through quarantine apparatus includes: a first sterilizer for
(Continued)

providing low-temperature plasma and ultraviolet rays; a thermal imaging camera configure to measure an amount of heat given off by a person; and a measurer configured to output the amount of heat given off by of a person as measured by the thermal imaging camera.

8 Claims, 3 Drawing Sheets

(51) Int. Cl.
    *A61L 2/00*     (2006.01)
    *A61L 2/14*     (2006.01)
    *A61L 2/26*     (2006.01)
    *A61L 9/20*     (2006.01)
    *A61L 9/22*     (2006.01)
    *E04H 1/12*     (2006.01)
    *H04N 23/23*     (2023.01)

(52) U.S. Cl.
    CPC ............ *A61L 2/26* (2013.01); *A61L 9/20* (2013.01); *A61L 9/22* (2013.01); *E04H 1/1277* (2013.01); *H04N 23/23* (2023.01); *A61L 2202/11* (2013.01); *A61L 2202/122* (2013.01); *A61L 2202/14* (2013.01); *A61L 2202/25* (2013.01); *A61L 2209/111* (2013.01)

(58) Field of Classification Search
    CPC ........... A61L 2209/111; A61L 2202/14; A61L 2202/25; A61B 5/015; H04N 23/23; E04H 1/1277
    See application file for complete search history.

(56) References Cited

FOREIGN PATENT DOCUMENTS

| | | |
|---|---|---|
| CN | 111364811 A | 7/2020 |
| KR | 10-2012-0026151 A | 3/2012 |
| KR | 10-2012-0113324 A | 10/2012 |
| KR | 10-1222637 B1 | 1/2013 |
| KR | 10-2013-0090961 A | 8/2013 |
| KR | 10-2014-0026050 A | 3/2014 |
| KR | 10-1571157 B1 | 11/2015 |
| KR | 10-1624697 B1 | 5/2016 |
| KR | 10-2020-0076163 A | 6/2020 |
| WO | 2015/009344 A1 | 1/2015 |

OTHER PUBLICATIONS

Extended European Search Report issued in U.S. Appl. No. 18/004,259 by the European Patent Office on Jul. 19, 2024, which is related to U.S. Appl. No. 18/004,259.

An Office Action mailed by China National Intellectual Property Administration on Jun. 30, 2025, which corresponds to Chinese Patent Application No. 202180048098.6 and is related to U.S. Appl. No. 18/004,259.

\* cited by examiner

WALK-THROUGH QUARANTINE APPARATUS

CROSS-REFERENCE TO RELATED APPLICATIONS

This application is the U.S. National Stage of International Application No. PCT/KR2021/007211 filed Jun. 9, 2021, which claims benefit of priority to Korean Patent Application No. 10-2020-0085170 filed Jul. 10, 2020, the entire content of which is incorporated herein by reference.

BACKGROUND

Field

The present disclosure relates to a walk-through quarantine apparatus installed in passenger gateway facilities, such as airports, ports, and terminals, to sterilize passenger's bodies and belongings.

RELATED ART

Since the early 2000s, epidemics of infectious diseases such as SARS, AI, Ebola, and MERS have occurred continuously. The epidemics have caused enormous human casualties and economic losses worldwide. In addition, the recent COVID-19 virus has come as an unprecedented infectious disease crisis to mankind, and as a result, the importance of disease prevention has further increased.

For example, an airport, which is the front-line gateway of a country, is a place that serves as a medium to introduce and spread infectious diseases. Thus, it is required to conduct a thorough quarantine inspection and quarantine system to block the spread of infectious diseases. Usually, when passengers enter and leave a country through an airport, they need to stand at long queues at the immigration control, customs, and quarantine points. When there are many passengers, the queues are endless at these points, which can cause problems in managing the passenger flow inside the airport. However, due to limitations of quarantine technologies and a lack of quarantine personnel, suspected infected people may pass through the departure and arrival halls without any sanctions at the airport quarantine stage, resulting in the spread of infectious diseases. In addition, an existing quarantine procedure, which is performed only by the quarantine personnel, has a disadvantage in that it takes a relatively long time.

In this situation, there is a need for an effective quarantine system that can reduce the waiting time of passengers to pass through the quarantine procedure and reduce the burden of the quarantine personnel by installing an apparatus for automatically quarantine airport passengers and baggage.

In addition, when the existing quarantine personnel directly conduct quarantine, there may be a possibility of infection to the quarantine personnel. This is why a quarantine system capable of quarantine without direct face-to-face is demanded.

In addition, infectious agents, which cause infectious diseases, exist in various forms such as bacteria, viruses, protozoa, fungi, and parasites, and a different quarantine method may be required for each infectious agent to achieve optimal efficiency. If only a specific infectious agent is focused in quarantine, a situation may arise in which the spread of other infectious agents cannot be adequately coped with. Therefore, there is a need for a multi-stage quarantine apparatus capable of satisfying quarantine requirements for various infectious agents at once, there is no such apparatus so far.

The place where such requirements are necessary is not limited to airports. As similar examples, passenger gateway facilities such as ports, train stations and bus terminals may be included. Furthermore, in a crisis situation where it is determined that a pandemic has occurred, multi-use facilities such as large-scale shopping malls, marts, exhibition halls, and concert halls with large crowds may also be considered places to install the quarantine apparatus.

The above background art is possessed or acquired by the inventor in the process of deriving the disclosure of the present application, and it cannot necessarily be said to be known art disclosed to the public prior to the present application.

SUMMARY

An aspect of the present disclosure provides a walk-through quarantine apparatus that uses a plurality of sterilizers to quarantine people passing through passenger gateway facilities and belongings thereof so as to prevent infectious diseases.

Objects to be solved in the embodiments are not limited to the object mentioned above, and other objects not mentioned will be clearly understood by those skilled in the art from the description below.

A walk-through quarantine apparatus according to an embodiment will be described.

The walk-through quarantine apparatus includes: a housing provided with an entrance and an exit, and having therein a passage through which passengers pass through; a first sterilizer provided at the entrance, and comprising a first plasma provider configured to provide plasma to an inside of the housing and a first UV radiating unit configured to radiate UV to the inside of the housing; a third sterilizer provided at the exit, and comprising a second plasma provider configured to provide plasma to the inside of the housing and a second UV radiating unit configured to radiate UV to the inside of the housing; and a second sterilizer provided between the first sterilizer and the third sterilizer in the housing, and formed in a negative pressure space than the first and third sterilizers.

According to one aspect, the first UV radiator and the second UV radiator may each include an LED that generates UV rays.

According to one aspect, the first plasma provider may generate lower-temperature plasma than plasma provided by the second plasma provider.

According to one aspect, the first sterilizer and the third sterilizer may each include a temperature controller for adjusting temperature of plasma.

According to one aspect, the second sterilizer may include a blower fan provided at a top of the housing to blow air into the housing and a suction module positioned at a bottom of the housing to suck air inside the housing.

According to one aspect, the second sterilizer may further include a side fan provided at a side surface of the housing to blow air into the housing.

According to one aspect, the second sterilizer may further include a negative pressure controller for controlling internal air pressure of the second sterilizer to block the air of the first sterilizer from being introduced into the third sterilizer.

According to one aspect, the walk-through quarantine apparatus may include a thermal imaging camera provided at the entrance and configured to capture a thermal image, and a measurer configured to outputting an amount of heat given off by a passenger as measured by the thermal imaging camera.

As described above, according to the present embodiment, since a plurality of sterilizers is provided, it is possible to prevent the spread of an infectious disease by disinfecting people and belongings passing through the passenger gateway facilities.

Effects of the walk-through quarantine apparatus according to an embodiment are not limited to the effect mentioned above, and other effects not mentioned will be clearly understood by those skilled in the art from the description below.

DESCRIPTION OF EXEMPLARY EMBODIMENTS

Figure 1:
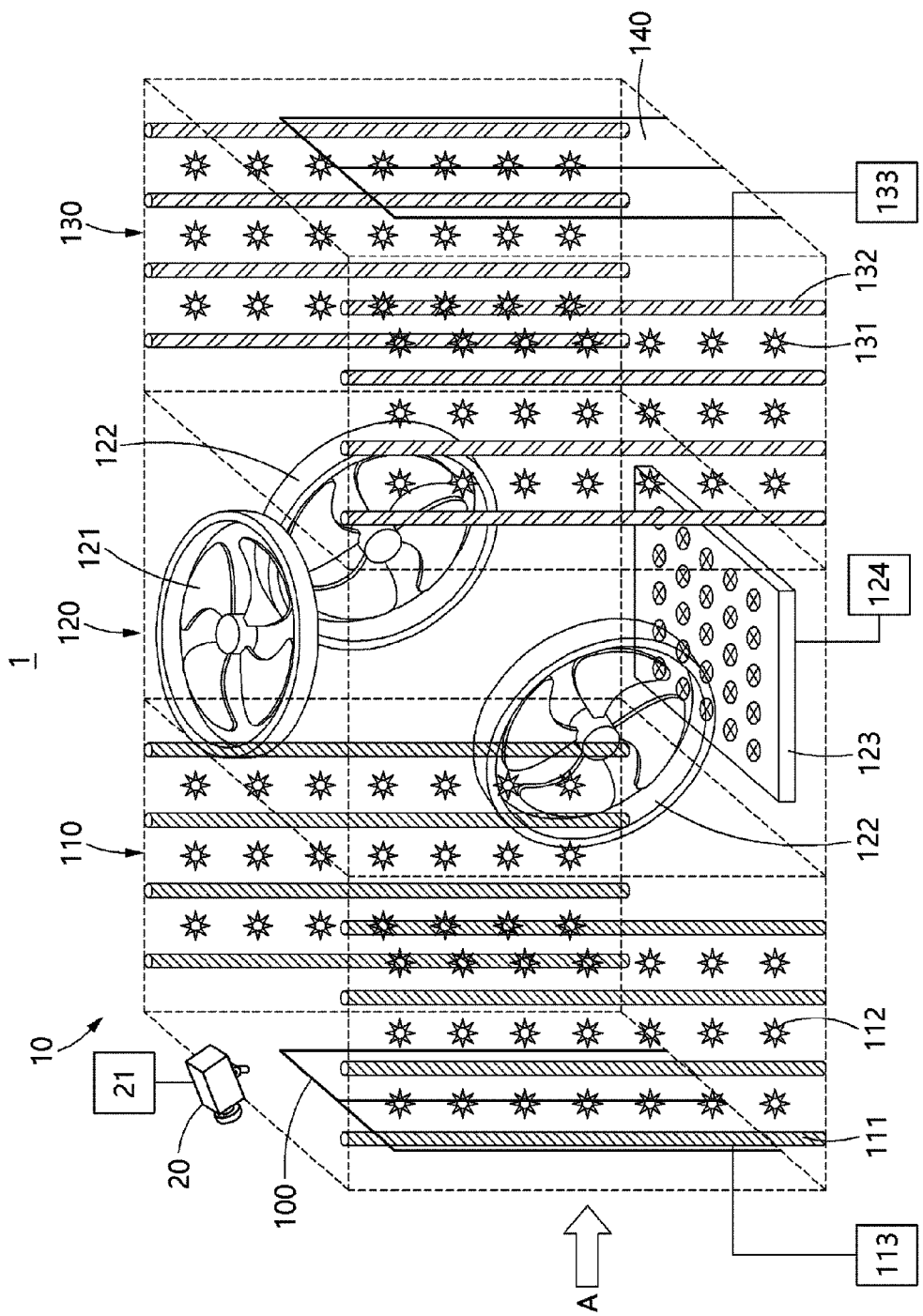
FIG. 1 is a perspective view of a walk-through quarantine apparatus according to an embodiment.

Hereinafter, embodiments will be described in detail with reference to the accompanying drawings. The present disclosure may include various modifications and embodiments, and therefore, the scope of the present disclosure is not restricted or limited by exemplary embodiments. It should be understood that all changes, equivalents or substitutes to the embodiments are included within the spirit and scope of the present disclosure.

Terms used in the examples are used only for descriptive purposes and should not be construed as limiting. Unless stated otherwise, an expression of singularity is intended to include expressions of plurality. In this specification, the term "comprise" or "have" is intended to designate characteristic, numbers, steps, operations, elements, components, or combinations thereof, but it is not intended to preclude the presence or addition of one or more other features, numbers, steps, operations, elements, components, or combinations.

Unless otherwise defined, all terms used herein including the technical or scientific terms have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

Additionally, terms such as first, second, A, B, (a), (b), etc. are used to describe elements of the present disclosure. These terms are only used to distinguish corresponding elements from other elements and the nature, order or sequence of the elements should not be limited by the terms. When an element is "connected", "coupled", or "linked" to another element, it is to be noted that the element may be directly connected or linked to the another element, but the element may be "connected", "coupled", or "linked" to the another element via another element therebetween.

An element described in any one of the example embodiments and an element including a common function or feature will be described using the same names in other example embodiments. Unless otherwise stated, the description in any one of the example embodiments may be applicable to other example embodiments, and a detailed description will be omitted in an overlapping range.

Figure 2:
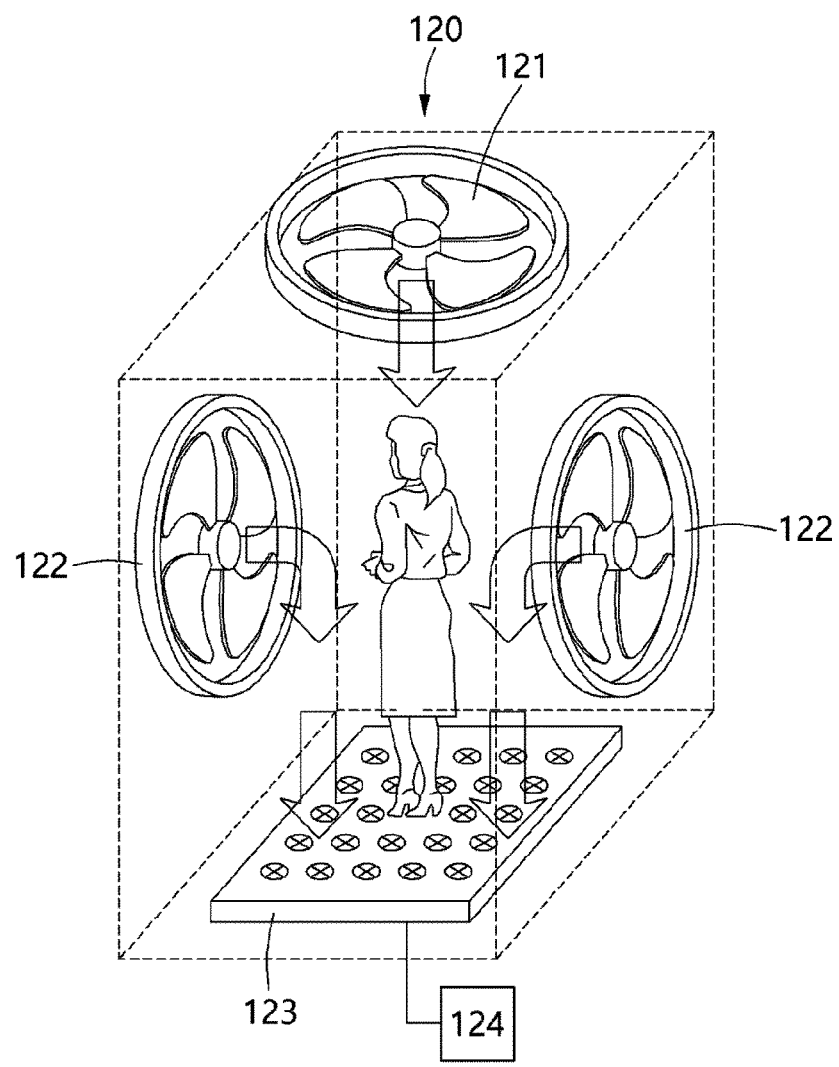
FIG. 2 is a perspective view of a second sterilizer in the walk-through quarantine apparatus of FIG. 1.
Figure 3:
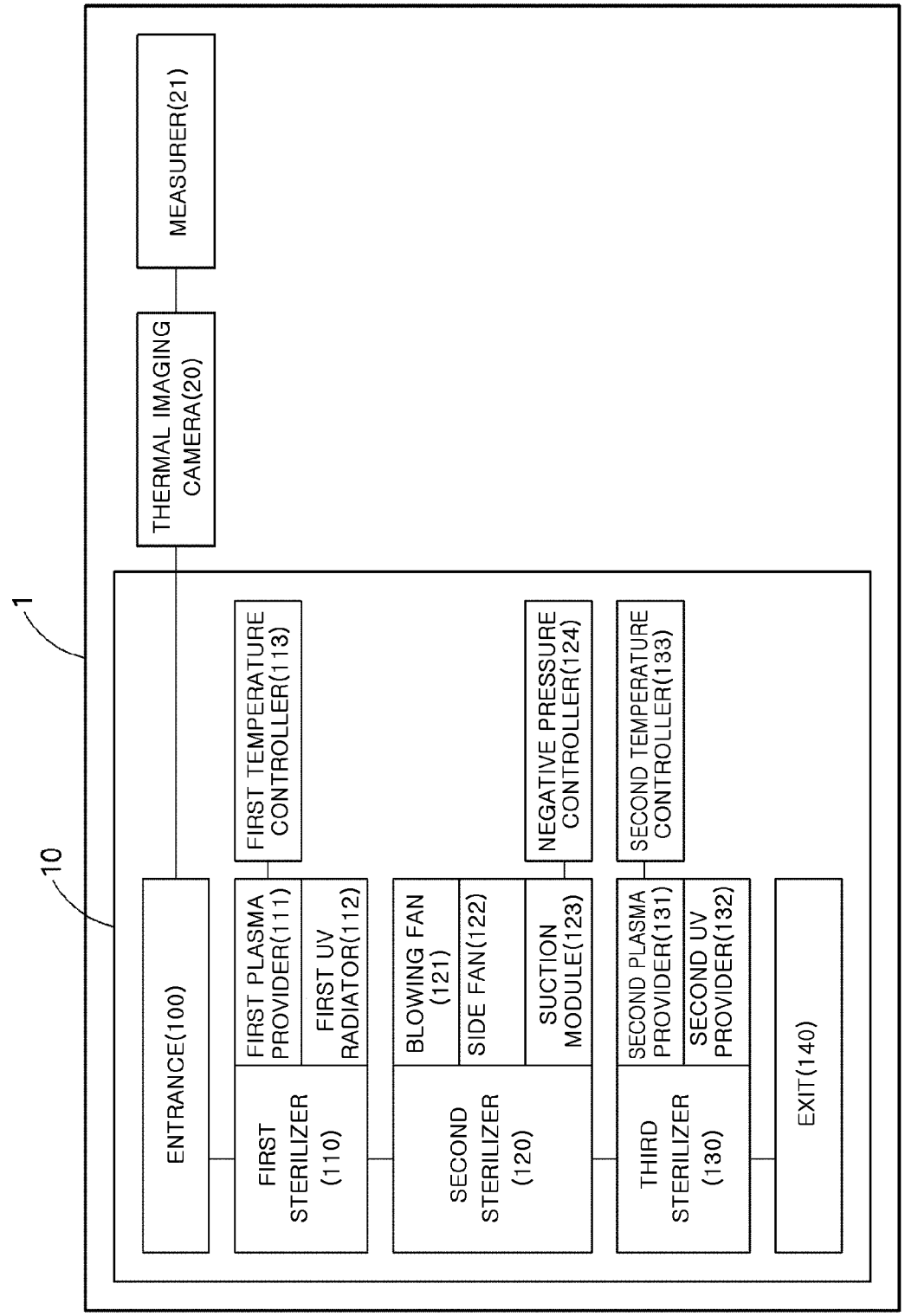
FIG. 3 is a block diagram showing a configuration of a walk-through quarantine apparatus according to an embodiment.

Hereinafter, a walk-through quarantine apparatus 1 will be described in detail with reference to FIGS. 1 to 3. FIG. 1 is a perspective view of a walk-through quarantine apparatus 1 according to an embodiment; FIG. 2 is perspective view of a second sterilizer 120 viewed from "A" direction in the walk-through quarantine apparatus 1 of FIG. 1; and FIG. 3 is a block diagram showing a configuration of the walk-through quarantine apparatus 1 according to an embodiment.

Referring to the drawings, the walk-through quarantine apparatus 1 may be installed and used in the arrival hall and departure hall of an airport. While passengers walk through the walk-through quarantine apparatus 1, the walk-through sterilization device 1 may sterilize the passengers in multiple stages by providing low-temperature plasma and ultraviolet sterilization, air sterilization, high-temperature plasma and ultraviolet sterilization. Here, the walk-through quarantine apparatus 1 may include personal luggage possessed by the passengers as well as the passengers.

The walk-through quarantine apparatus 1 includes a housing 10, a first sterilizer 110, a second sterilizer 120, and a third sterilizer 130.

The housing 10 has an entrance 100 and an exit 140, has a tunnel shape, provides a passage for passengers to pass through, and is provided with a plurality of sterilization units to sterilize passengers and luggage while passengers pass through the housing 10.

Here, the shape of the housing 10 is not limited by the drawings, and may substantially have a variety of shapes including a rectangular parallelepiped cylinder shape, and the shape and size of the housing 10 may be appropriately applied in consideration of an installation environment and the like.

The first sterilizer 110 is installed at the entrance 100 of the housing 10, and primarily sterilizes passengers passing through the walk-through quarantine apparatus 1. The first sterilizer 110 includes a first plasma provider 111, a first UV radiator 112, and a first temperature controller 113.

The first plasma provider 111 provides low-temperature plasma to the first sterilizer 110. Here, the first plasma provider 111 sterilizes the first sterilizer 110 by ion clusters included in the low-temperature plasma. In addition, since the first plasma provider 111 performs sterilization at a relatively low temperature of 50 degrees or less, sterilization may be possible without causing inconvenience to passengers and may be performed even for products that are vulnerable to heat.

Here, the first plasma provider 111 is illustrated as being installed at a sidewall of the first sterilizer 110, but this is only an example, and the first plasma provider 111 may be installed not just at the sidewall of the first sterilizer 110, but the position of installation of the first plasma provider 111 may substantially vary, including an upper wall or an entire wall surface of the first sterilizer 110.

The first UV radiator 112 includes a light emitting diode (LED).

The first UV radiator 112 generates short-wavelength ultraviolet rays having strong sterilization power. By radiating the short-wavelength ultraviolet rays, the first UV radiator 112 may effectively sterilize passengers and bacteria, fungi, microorganisms, viruses, and the like present in the first sterilizer 110.

Here, the first UV radiator 112 is illustrated as being installed at the sidewall of the first sterilizer 110, but this is only an example, and the position and arrangement of the first UV radiator 112 may substantially vary.

For reference, a plasma sterilization method is an indirect sterilization method in which charged particles act in the air to remove bacteria and viruses, thereby enabled to continuously sterilizing a wide space. In addition, the UV sterilization method is a direct sterilization method in which short-wavelength ultraviolet rays directly act, thereby enabling a short-term sterilization effect in a small space. According to this embodiment, the first sterilizer 110 may produce an optimal sterilization effect by simultaneously performing two types of sterilization, i.e., providing plasma and radiating UV rays.

The second sterilizer 120 is provided between the first sterilizer 110 and the third sterilizer 130 in the housing 10, and secondarily sterilizes passengers who have passed through the first sterilizer 110 and sterilize by providing air.

The second sterilizer 120 may include a blower fan 121, a side fan 122, a suction module 123, and a negative pressure controller 124.

The blower fan 121 is provided at a top of the housing 10 and blows air from the top to the bottom toward a passenger to remove dust or contaminants attached to the passenger or luggage.

The side fan 122 is provided at a side wall of the housing 10 to blow air toward a passenger.

The suction module 123 is provided at a bottom of the housing 10 to suck air from the inside of the second sterilizer 120 and discharge the air to the outside.

In the second sterilizer 120, air generated from the blower fan 121 and the side fan 122 removes dust or contaminants attached to a passenger or luggage, and the air containing the dust and contaminants separated from the passenger and luggage is not diffused to the surroundings, but discharged by the suction module 123 to the outside in a downward direction.

Although not shown in the drawing, the suction module 123 may include a filter or dust collector to remove the dust or contaminant from the sucked air.

The second sterilizer 120 may more effectively remove dust or contaminants attached to passengers and luggage by spraying air to the top and sides of passengers. Accordingly, in the second sterilizer 120, the positions of the blower fan 121, the side fan 122, and the suction module 123 may be determined so as to form the most efficient air flow in consideration of an internal environment and an air flow.

In addition, the second sterilizer 120 directs the flow of air blown from the blower fan 121 and the side fan 122 downward, so that the second sterilizer 120 is separated from the first sterilizer 110 and the third sterilizer 130 aerodynamically 130.

The negative pressure controller 124 maintains the inside of the second sterilizer 120 at negative pressure so as to prevent the flow of air inside the second sterilizer 120 to the first sterilizer 110 and the third sterilizer 130.

By maintaining the internal pressure of the second sterilizer 120 lower than the internal pressure of the first sterilizer 110 and the third sterilizer 130, the negative pressure controller 124 may prevent the internal air of the second sterilizer 120 from escaping to the first sterilizer 110 and the third sterilizer 130.

The third sterilizer 130 is provided at the exit 140 of the housing 10 and tertiarily sterilizes a passenger passing through the walk-through quarantine apparatus 1.

The third sterilizer 130 may include a second plasma provider 131, a second UV radiator 132, and a second temperature controller 133.

The second plasma provider 131 provides high-temperature plasma to the third sterilizer 130.

The temperature of the second plasma may be controlled by the second temperature controller 133. However, maintaining the second plasma at a higher temperature than that of the first plasma may be more effective in terms of the disease prevention effect. Here, the third sterilizer 130 provides a high-temperature plasma, and thus, a sterilization effect can be expected through instantaneous high-temperature heat generation of the plasma.

Here, the second plasma provider 131 is illustrated as being installed at a sidewall of the third sterilizer 130, but this is only an example, and the second plasma provider 131 may be installed not only at the side wall of the third sterilizer 130 and the position of installation of the third sterilizer 130 may vary, including an upper wall surface or the entire wall surface of the third sterilizer 130.

The second UV radiator 132 includes a light emitting diode (LED).

The second UV radiator 132 generates short-wavelength ultraviolet rays having strong sterilizing power. By radiating the short-wavelength ultraviolet rays, the second UV radiator 132 can effectively sterilize passengers and bacteria, fungi, microorganisms, and viruses present in the third sterilizer 130.

Here, the second UV radiator 132 is illustrated as being installed at a sidewall of the third sterilizer 130, but this is only an example, and the position and arrangement of the second UV radiator 132 may substantially vary.

Through simultaneous sterilization using high-temperature plasma and UV rays, the third sterilizer 130 may finally sterilize and remove germs, microorganisms, and contaminated air present in an object passing through the third sterilizer 130.

In the walk-through quarantine apparatus 1, a thermal imaging camera 20 and a measurer 21 may be provided at the entrance 100.

The thermal imaging camera 20 and the measurer 21 may measure a calorific value before a passenger enters the walk-through quarantine apparatus 1, and may provide a result of measurement to a quarantine officer in real time. For example, the main symptom of the Covid virus, which is currently in a global pandemic, is fever. In this embodiment, by using the thermal imaging camera 20 and the measurer 21, it is possible to separately screen out a suspected infected person passing through the walk-through quarantine apparatus 1, thereby preventing the spread of infection. Furthermore, it is possible to prevent secondary infection after a suspected infected person enters or leaves a country.

According to these embodiments, while a passenger passes through the first sterilizer 110, the second sterilizer 120, and third sterilizers 130, the walk-through quarantine apparatus 1 performs sterilization in multiple stages by spraying plasma, UV rays, and air. In addition, the walk-through sterilization device 1 radiates low-temperature plasma and UV rays for primary sterilization, sprays air for secondary sterilization, and radiates high-temperature plasma and UV for tertiary sterilization, whereby an effective and strong sterilization effect can be expected. In addition, using a walk-through method, it is possible to carry out quarantine quickly and efficiently without a waiting time. In addition, the walk-through quarantine apparatus 1 may determine whether or not a passenger is infected through the thermal imaging camera 20 and the measurer 21, and may prevent a possibility of contamination of the walk-through quarantine apparatus 1 in advance.

Meanwhile, the walk-through quarantine apparatus 1 may include a controller (not shown) that controls the operation of the first sterilizer 110, the second sterilizer 120, and the third sterilizer 130 by detecting a quarantine status inside the housing 10 and a number of passenger populations. Through the controller (not shown), the operation of the walk-through quarantine apparatus 1 may be remotely controlled according to the number of passenger population.

In addition, the housing 10 may be formed to assemble and disassemble a plurality of sterilizers, thereby enabled to be expandable. A connecting portion (not shown) for connecting the connected sterilizers to each other may be provided at portions where the first sterilizer 110, the second sterilizer 120, and third sterilizers 130 are coupled. For example, as in the above-described embodiment, in an assembly in which the first sterilizer 110, the second sterilizer 120, and third sterilizers 130 are assembled one by one, an additional sterilizer may be added through connecting portions (not shown) on an outer side of the first sterilizer 110 and an outer side of the third sterilizer 130. Alternatively, two or more of the first sterilizer 110, the second sterilizer 120, and third sterilizers 130 may be arranged and assembled. In addition, if necessary, the number of the first sterilizer 110, the second sterilizer 120, and third sterilizers 130 may be appropriately added or changed.

In addition, at a bottom of the walk-through quarantine apparatus 1, a wheel portion (not shown) to enable movement of the housing 10 may be provided. For example, the wheel portion (not shown) is provided at the bottom of the housing 10 so that the walk-through quarantine apparatus 1 can be moved to and installed at a required location.

According to the present embodiments, since the walk-through quarantine apparatus 1 employs a walk-through method, it is possible to carry out quarantine inspection quickly and efficiently without a waiting time.

In addition, since sterilization is performed in multiple stages by a plurality of sterilization means in the walk-through quarantine apparatus 1, a better sterilization effect may be achieved compared to the case of direct sterilization by quarantine personnel, and various infectious agents rather than a specific infectious agent may be inspected at the same time.

In addition, using the thermal imaging camera 20 and the measurer 21, it is possible to identify a suspected infected person in advance before entry into the walk-through quarantine apparatus, and to prevent the person from entering the walk-through quarantine apparatus.

In addition, as the walk-through quarantine apparatus 1 is of an assemblable module type, an additional configuration may be added according to the type of infectious diseases.

In addition, it is easy to install, remove, and move the walk-through quarantine apparatus 1, so the walk-through quarantine apparatus 1 may be applied to places in various environments.

Meanwhile, in the above-described embodiments, a case where the walk-through quarantine apparatus 1 is applied at an airport has been described as an example, but the walk-through quarantine apparatus may also be installed in and applied to shopping malls, marts, exhibition halls and concert halls with a large population.

Although the present inventive concept has been described with reference to a limited number of exemplary embodiments and drawings, one of ordinary skill in the art would be capable of amending and modifying based on the description above. Appropriate results may be obtained even when, for example, the above-described methods are performed in a different order from the description above, and/or the above-described elements, such as systems, structures, devices, and circuits, are combined in a manner different from the description above or replaced with substitutions or equivalents.

Therefore, the scope of the present disclosure is not limited to the above-described exemplary embodiments, but by the appended claims, and all differences within the scope will be construed as being included in the present disclosure.

What is claimed is:

1. A walk-through quarantine apparatus comprising:
a housing provided with an entrance and an exit, and having therein a passage through which passengers pass through;
a first sterilizer provided at the entrance, and comprising a first plasma provider configured to provide plasma to an inside of the housing and a first UV radiating unit configured to radiate UV to the inside of the housing;
a third sterilizer provided at the exit, and comprising a second plasma provider configured to provide plasma to the inside of the housing and a second UV radiating unit configured to radiate UV to the inside of the housing; and
a second sterilizer provided between the first sterilizer and the third sterilizer in the housing, and formed in a negative pressure space than the first and third sterilizers.

2. The walk-through quarantine apparatus of claim 1, wherein the first UV radiator and the second UV radiator comprise LEDs that generate UV.

3. The walk-through quarantine apparatus of claim 1, wherein the first plasma provider generates lower-temperature plasma than the plasma provided by the second plasma provider.

4. The walk-through sterilization device of claim 3, wherein the first sterilizer and the third sterilizer comprise a temperature controller for adjusting temperature of plasma.

5. The walk-through sterilization device of claim 1, wherein the second sterilizer comprises: a blower fan provided at a top of the housing to blow air to the housing; and a suction module positioned at a bottom of the housing to suck air inside the housing.

6. The walk-through quarantine apparatus of claim 5, wherein the second sterilizer further comprises a side fan provided on a side surface of the housing to blow air into the housing.

7. The walk-through quarantine apparatus of claim 5, wherein the second sterilizer further comprises a negative pressure controller configured to control internal air pressure of the second sterilizer to block air from the first sterilizer from being introduced into the third sterilizer.

8. The walk-through quarantine apparatus of claim 1, further comprising:
a thermal imaging camera provided at the entrance and configured to capture a thermal image; and a measurer configured to output an amount of heat given off by a passenger as measured by the thermal imaging camera.

\* \* \* \* \*